(12) United States Patent
Shibamoto et al.

(10) Patent No.: US 8,329,843 B2
(45) Date of Patent: Dec. 11, 2012

(54) METHOD FOR PRODUCING AMIDE COMPOUND

(75) Inventors: Hiroko Shibamoto, Ichihara (JP); Toshikazu Aikawa, Mobara (JP); Teruo Arii, Chiba (JP); Masanori Muramoto, Takaishi (JP); Takeshi Fukuda, Takaishi (JP); Kiyoshi Ito, Suginami-ku (JP); Takeya Abe, Takaishi (JP); Souichi Hazama, Izumi (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 13/197,066

(22) Filed: Aug. 3, 2011

(65) Prior Publication Data

US 2011/0288255 A1 Nov. 24, 2011

Related U.S. Application Data

(62) Division of application No. 12/089,511, filed as application No. PCT/JP2006/320087 on Oct. 6, 2006, now abandoned.

(30) Foreign Application Priority Data

Oct. 7, 2005 (JP) ................................. 2005-295561
Dec. 27, 2005 (JP) ................................. 2005-375024

(51) Int. Cl.
C12P 13/00 (2006.01)
C08F 20/02 (2006.01)

(52) U.S. Cl. ..................................... 526/303.1; 435/129
(58) Field of Classification Search ............... 526/303.1; 435/129
See application file for complete search history.

(56) References Cited

U.S. PATENT DOCUMENTS

| | | | |
|---|---|---|---|
| 2,622,097 | A | 12/1952 | Osborne |
| 5,292,919 | A | 3/1994 | Himes et al. |
| 5,426,208 | A | 6/1995 | Himes et al. |
| 5,552,305 | A | 9/1996 | Fallon et al. |
| 6,043,061 | A | 3/2000 | Ishii et al. |
| 6,074,532 | A * | 6/2000 | Patel et al. ............ 203/6 |
| 6,228,633 | B1 * | 5/2001 | Oriel et al. ............ 435/232 |
| 6,780,289 | B2 | 8/2004 | Godbole |
| 7,575,912 | B2 | 8/2009 | Hughes et al. |
| 2002/0043455 | A1 | 4/2002 | Godbole |
| 2003/0104586 | A1 | 6/2003 | Abe et al. |
| 2004/0048348 | A1 | 3/2004 | Murao et al. |
| 2007/0027294 | A1 | 2/2007 | Murao et al. |
| 2007/0077634 | A1 | 4/2007 | Hughes et al. |
| 2009/0269822 | A1 | 10/2009 | Hughes et al. |

FOREIGN PATENT DOCUMENTS

| | | |
|---|---|---|
| JP | 5-308980 A | 11/1993 |
| JP | 7-145123 | 6/1995 |
| JP | 7-265090 A | 10/1995 |
| JP | 7-265091 A | 10/1995 |
| JP | 9-227478 A | 9/1997 |
| JP | 10-316714 | 12/1998 |
| JP | 11-123098 A | 5/1999 |
| JP | 2002-80443 A | 3/2002 |
| JP | 2004-350573 A | 12/2004 |
| WO | WO 93/23366 | 11/1993 |
| WO | WO 02/50297 | 6/2002 |
| WO | WO 2004/090148 A1 | 10/2004 |
| WO | WO 2005/054456 | 6/2005 |

OTHER PUBLICATIONS

International Search Report dated Nov. 28, 2006.
Jun Sik Hwang et al., Department of Chemical Engineering, Korea Advanced Institute of Science and Technology, Biotransformation of Acrylonitrile to Acrylamide Using Immobilized Whole Cells of *Brevibacterium* CH1 in a Recycle Fed-Batch Reactor, Biotechnology and Bioengineering, 1989, vol. 34, pp. 380-386.
Office Action issued in corresponding Australian Patent Application No. 2005300431 dated Dec. 11, 2009.
Dia-Nitrix Co., Ltd. Acrylonitrile Product Specification.
INEOS Nitriles Acrylonitrile Specification Tests: Organic Impurities by Gas Chromatography (9 Pages) Jun. 7, 2001.
INEOS Nitriles Acetonitrile Specification Tests: Organic Impurities by GC (11 Pages) Apr. 1, 2008.
Gao et al., *Inhibition and deactivation of nitrile hydratase in the production of acrylamide*, Guocheng Gongcheng Xuebao, Circa 2005, 5923), 193-196; as abstracted by CAPlus AN 2005:469375, 1 Page.
Supplementary European Search Report mailed on Feb. 15, 2012, issued in related application EP 06811414.9.
M, Kobayashi et al., *Enzymatic synthesis of acrylamide: a success story not yet over*, 10(1) Trends in Biotechnology 402-408 (Jan. 1, 1992).
T. Nagasawa et al., *Microbial transformations of nitriles*, 7(6) Trends in Biotechnology 153-158 (Jun. 1, 1989).

* cited by examiner

*Primary Examiner* — Ling Choi
*Assistant Examiner* — Chun-Cheng Wang
(74) *Attorney, Agent, or Firm* — Buchanan Ingersoll & Rooney PC

(57) ABSTRACT

A method for producing an amide compound from a nitrile compound in an aqueous medium in the presence of a catalyst having a nitrile hydratase activity wherein the concentration of benzene in the aqueous medium is 4.0 ppm or less and a method for producing an amide-based polymer excellent in quality from the amide compound. Also provided are a method for more efficiently producing an acrylamide with higher quality by a microbial catalyst containing a nitrile hydratase and the like and a method for producing an acrylamide-based polymer, which is excellent in hue, has a good balance between water solubility and high molecular weight and is excellent in quality.

2 Claims, No Drawings

METHOD FOR PRODUCING AMIDE COMPOUND

The present application is a Divisional Application of U.S. patent application Ser. No. 12/089,511, filed Apr. 7, 2008, which is a National Stage Application of PCT/JP2006/320087, filed Oct. 6, 2006, and claims priority to Japanese Patent Application No. 2005-295561, filed Oct. 7, 2005, and Japanese Patent Application No. 2005-375024, filed Dec. 27, 2005, the entire contents of each of which are incorporated by reference herein.

TECHNICAL FIELD

The present invention relates to a method for producing an amide compound.

The present invention (the first invention) relates more particularly to methods for producing an amide compound and an amide-based polymer and further more particularly to a method for efficiently producing a corresponding amide compound from a nitrile compound in an aqueous medium by the use of a catalyst having a nitrile hydratase activity, and a method for producing an amide-based polymer of high quality from the amide compound. In addition, the present invention (the second invention) relates more particularly to methods for producing an acrylamide and an acrylamide-based polymer and further more particularly to a method for producing an acrylamide of high quality by hydrating an acrylonitrile using a microbial cell containing a nitrile hydratase and the like; and to a method for producing an acrylamide-based polymer of high quality from the acrylamide.

BACKGROUND ART

As mentioned below, various production methods have been disclosed for industrially useful amide compounds.

Recently, there have been discovered nitrile hydratases having a nitrile hydration activity capable of converting a nitrile group into an amide group through hydration and there has been already disclosed a method for producing a corresponding amide compound from a nitrile compound by the use of the enzyme, a microbial cell containing the enzyme, or the like. The production method is known to have benefits such as a high conversion and a high selectivity from the nitrile compound to the corresponding amide compound, compared to the conventional scientific methods.

In industrially producing an amide compound by using these nitrile hydratases, it is important to maximize the amide compound productivity of the nitrile hydratases as catalysts (the number of molecules of the amide compound produced per one molecule of the nitrile hydratase). For this reason, numerous proposals have been made for the purposes of maintaining and increasing the enzyme activity, preventing the activity deterioration, recovering the deteriorated enzyme activity and the like. For example, it is well known that the enzyme activity is maintained and increased by contacting a microbial cell containing a nitrile hydratase or a processed product of the microbial cell with an oxidant in the conditions where the cells are not allowed to grow (see Patent Document 1). Further, it is well known that the activity deterioration of a nitrile hydratase is prevented by using a nitrile compound in which the concentration of the contained hydrocyanic acid is reduced (see Patent Document 2). In addition, there are known a method in which the reaction is carried out by using a microbial cell crosslinked with glutaraldehyde (see Patent Document 3), a method in which the reaction is carried out in the presence of a higher unsaturated fatty acid or its salt (see Patent Document 4), a method in which the reaction is carried out by using a microbial cell processed with an organic solvent or a processed product thereof (see Patent Document 5), and the like. The above is the background art of the first invention.

Further, as mentioned above, one of the main methods for producing acrylamide is a method of hydrating acrylonitrile. For example, there is known a method of hydrating acrylonitrile with a metallic copper catalyst such as Raney copper or the like or a method of hydrating acrylonitrile by using a microbial cell containing a nitrile hydratase, a processed product of the microbial cell, or the like as a catalyst.

Among these, as an industrial production method, the method for producing acrylamide using the microbial cell containing the nitrile hydratase or the like as a catalyst, has attracted attention because the method has a high conversion and a high selectivity of acrylonitrile, compared to the conventional method of hydration using the metallic copper catalyst and the like.

In order to efficiently produce acrylamides with higher quality by using the microbial cell containing the nitrile hydratase, and the like as a catalyst, impurities inhibiting the catalytic action of the microbial cell and the like are required to be removed as much as possible.

In addition, acrylamides obtained by such reactions are mainly used as a raw material for an acrylamide-based polymer. However, recently a further improvement of the quality is required for the acrylamide-based polymer. For example, the applications of an acrylamide-based polymer include a flocculant. Recently, the acrylamide-based polymer used as a flocculant is expected to have a higher molecular weight while maintaining the water solubility to improve the performance. Further, the acrylamide-based polymer is used as an additive for manufacturing paper, and the like, and, as the additive for manufacturing paper, a polymer being more excellent in hue is required in order to further improve the quality of the resulting paper.

As a method for improving the quality of the acrylamide obtained with use of cellular catalysts containing the nitrile hydratase, and the like or the quality of the polyacrylamide, as mentioned above, there are known a method in which the concentration of hydrocyanic acid in a nitrile compound is reduced by a chemical process and then the nitrile hydratase is allowed to act on the nitrile compound to produce an amide compound (for example, see Patent Document 2), and a method in which oxazole and hydrocyanic acid contained in acrylonitrile as impurities are reduced and then the acrylonitrile is converted into acrylamide, followed by producing an acrylamide-based polymer from the acrylamide (for example, see Patent Document 6). The above is the background art of the second invention.

[Patent Document 1] Japanese Patent Application Laid-Open Publication No. 2004-350573
[Patent Document 2] Japanese Patent Application Laid-Open Publication No. 11-123098
[Patent Document 3] Japanese Patent Application Laid-Open Publication No. H7-265091
[Patent Document 4] Japanese Patent Application Laid-Open Publication No. H7-265090
[Patent Document 5] Japanese Patent Application Laid-Open Publication No. H5-308980
[Patent Document 6] International Publication WO 2004/090148

DISCLOSURE OF THE INVENTION

Problems to be Solved by the Invention

However, the productivity of the amide compound using the nitrile hydratase is decreased due to other factors that are not be resolved by the conventional techniques described in the background art of the first invention, and it has also been desired to resolve the factors in order to efficiently produce the amide compound using the nitrile hydratase.

Accordingly, an object of the first invention is to provide a method for efficiently producing a corresponding amide compound from a nitrile compound by a reaction using a nitrile hydratase. In addition, another object of the first invention is to provide a method for producing an amide-based polymer with high quality using the amide compound produced by the above method.

Further, according to the methods described in the background art of the second invention, sufficient effects may not be always obtained from the viewpoints of eliminating a factor that inhibits the catalytic action of a microbial cell containing a nitrile hydratase and the like and efficiently performing hydration of acrylonitrile. In addition, there is still room for improvement from the viewpoint of improving the quality of the acrylamide and acrylamide-based polymer.

Therefore, an object of the second invention is to provide a method for more efficiently producing acrylamide with higher quality using a cellular catalyst containing a nitrile hydratase and the like and a method for producing an acrylamide-based polymer, which is excellent in hue, has a good balance between the water solubility and the high molecular weight and is also excellent in quality, by using the acrylamide.

Means for Solving the Problems

The present inventors have earnestly studied on the production method for an amide compound in order to solve the above problems of the first invention. The present inventors have found that, in a method for producing a corresponding amide compound from a nitrile compound in an aqueous medium using a catalyst having a nitrile hydratase activity, the amide compound may be efficiently produced without reducing the reaction rate of the nitrile hydratase when the concentration of benzene in the aqueous medium is reduced to a specific value or lower. In general, benzene in the aqueous medium is derived from the nitrile compound that is a raw material. Even when it is derived from other sources, the amide compound may be efficiently produced by reducing the concentration of benzene to the same level as the above. In addition, an amide-based polymer excellent in hue may be obtained by using the amide compound produced by the above method, under the reaction conditions in which the concentration of benzene is reduced as described.

That is, the first invention is as follows.

[1] A method for producing an amide compound from a nitrile compound in an aqueous medium in the presence of a catalyst having a nitrile hydratase activity, wherein the concentration of benzene in the aqueous medium is 4.0 ppm or less.

[2] The method for producing an amide compound described in [1] in which the nitrile hydratase is a microbe producing a nitrile hydratase derived from *Pseudonocardia* or *Rhodococcus*.

[3] The method for producing an amide compound described in [1] or [2] in which a nitrile compound is acrylonitrile or methacrylonitrile.

[4] A method for producing an amide-based polymer by homopolymerizing the amide compound described in [1] or by copolymerizing the amide compound and at least one unsaturated monomer copolymerizable with the amide compound.

[5] The method for producing an amide-based polymer described in [4] in which the amide compound is acrylamide or methacrylamide.

In addition, the present inventors have studied the problems of the second invention and found that the catalytic activity of a nitrile hydratase may be maintained and an acrylamide with high quality may be obtained by reducing the concentration of acrolein contained in an acrylonitrile, and further found that an acrylamide-based polymer which is excellent in hue and has a good balance between the water solubility and the high molecular weight may be obtained from the acrylamide, and thus accomplished the second invention.

In other words, the method for producing acrylamide of the second invention is characterized in that an acrylonitrile in which the concentration of acrolein is 1 ppm or less is hydrated in an aqueous medium with a microbial cell containing a nitrile hydratase or a processed product of the microbial cell.

The concentration of hydrocyanic acid contained in the above acrylonitrile is preferably 5 ppm or less.

Further, the concentration of oxazole contained in the acrylonitrile is also preferably 10 ppm or less.

Furthermore, it is also preferable that the concentration of hydrocyanic acid contained in the above acrylonitrile is 5 ppm or less and the concentration of oxazole contained in the above acrylonitrile is 10 ppm or less.

The method for producing an acrylamide-based polymer of the second invention is characterized in that the above acrylamide is homopolymerized or the above acrylamide is copolymerized with at least one unsaturated monomer copolymerizable with the acrylamide.

Effect of the Invention

According to the first invention, in the reaction using a nitrile hydratase, a corresponding amide compound may be efficiently produced from a nitrile compound by reducing the concentration of benzene in an aqueous medium containing the nitrile compound to the specific value or lower. In addition, an amide-based polymer excellent in hue may be obtained by using the amide compound produced by the above method, under the reaction conditions in which the concentration of benzene is reduced as described.

Further, according to the second invention, an acrylamide with higher quality may be more efficiently produced by a microbial catalyst containing a nitrile hydratase and the like. Furthermore, according to the second invention, there may be obtained an acrylamide-based polymer that is excellent in hue, has a good balance between the water solubility and the high molecular weight, and is also excellent in quality.

BEST MODE FOR CARRYING OUT THE INVENTION

1. The First Invention

Hereinafter, the first invention will be explained in detail.

A catalyst having a nitrile hydratase activity used in the first invention is a microbial cell producing a nitrile hydratase or a processed product of the microbial cell. The term "nitrile hydratase" here is a protein having an ability of hydrating a nitrile compound. The microbes producing a nitrile hydratase include microbes belonging to *Nocardia, Corynebacterium, Bacillus, thermophilic Bacillus, Pseudomonas, Micrococcus, Rhodococcus* represented by *rhodochrous* species, *Acinetobacter, Xanthobacter, Streptomyces, Rhizobium, Klebsiella, Enterobacter, Erwinia, Aeromonas, Citrobacter, Achromo-*

*bacter, Agrobacterium, Pseudonocardia* represented by *thermophila* species, *Bacteridium, Brevibacterium* and the like. Preferable are microbes belonging to *Pseudonocardia* and *Rhodococcus* and especially preferable are *Pseudonocardia thermophila* JCM3095 and *Rhodococcus rhodochrous* J-1.

Further, the microbes producing the nitrile hydratase in the first invention also include a transformant obtained by expressing a nitrile hydratase gene cloned from the above-mentioned microbe in an arbitrary host. The arbitrary hosts referred to herein are not particularly limited, and include *Escherichia coli* as a representative example as in the case of Examples described later, *Bacillus* such as *Bacillus subtilis* and the like and other macrobial strains such as yeasts, *Actinomyces* and the like. Examples thereof include MT-10822 (the strain deposited at National Institute of Bioscience and Human Technology, Agency of Industrial Science and Technology, Ministry of International Trade and Industry, 1-3, Higashi 1-chome, Tsukuba-shi, Ibaraki-ken, Japan on Feb. 7, 1996, under an accession number FERM BP-5785, under the terms of the Budapest Treaty on the International Recognition of the Deposit of Microorganisms for the Purposes of Patent Procedure). The microbes producing the nitrile hydratase in the first invention also include transformants expressing a mutant nitrile hydratase that are obtained by replacing, deleting, eliminating or inserting one or two or more of constituent amino acids of the enzyme with other amino acids by using recombinant DNA technology and thereby have been further improved in amide compound resistance, nitrile compound resistance and temperature resistance.

In using the microbe producing the nitrile hydratase in a production method of the first invention, the microbial cell or the processed product of the microbial cell is generally used. The microbial cell may be prepared by using a general method well known in the fields of molecular biology, bioengineering and genetic engineering. For example, there may be mentioned a method in which the microbe is planted in typical liquid culture mediums such as an LB medium, an M9 medium and the like and then is grown at an appropriate culture temperature (which is generally from 20° C. to 50° C., and may be 50° C. or higher in the case of a *thermophilic* bacterium), and the microbe is separated and recovered from the culture liquid using a centrifugal separation.

In addition, the processed products of the microbial cells are not particularly limited in the shape and include an extract and a ground product of the above microbial cell; a post-separated product obtained by separating and purifying a nitrile hydratase active fraction of the extract and the ground product; and an immobilized product obtained by immobilizing the microbial cell, or the extract, the ground product or the post-separated product of the microbial cell using an appropriate carrier. These are usable as the processed product of the microbial cell in the first invention as long as they have the nitrile hydratase activity.

The microbial cell producing the nitrile hydratase or the processed product of the microbial cell may be used for the reaction immediately after production, or may be stored after production and used as needed.

The microbial cell producing the nitrile hydratase or the processed product of the microbial cell in the first invention may be used in either a batch reaction or a continuous reaction. In addition, the reactor type may be selected from a suspended bed, a fixed bed, a fluidized bed or the like, depending on the form of the microbial cell or the processed product of the microbial cell. The concentration of catalyst in the reaction solution is not particularly limited as long as it does not disturb the mixing of an aqueous medium and the nitrile compound.

The aqueous medium in the first invention refers to water or an aqueous solution (the whole reaction solution) in which there are dissolved a buffer agent such as a phosphate or the like, an inorganic salt such as a sulfate, carbonate or the like, a hydroxide of alkali metal, the amide compound, the nitrile compound, the catalyst having a nitrile hydratase activity or the like at a suitable concentration. In the first invention, even if the reaction is carried out in a homogeneous system in which the concentration of the nitrile compound in the aqueous solution is less than a saturated concentration or in a two-phase system consisting of a nitrile phase and a water phase in which system the concentration of the nitrile compound is at a saturated concentration or more, the whole solution is defined as the aqueous medium. Further, in the present specification, the aqueous medium in the first invention is also referred to as "the aqueous medium (I)". In the case of the two-phase system where two phases are separated under static conditions, it is important to sufficiently mix the water phase and the nitrile phase by using a suitable mixing apparatus such as a rotary blade, a line mixer or the like.

In the first invention, the concentration of the nitrile compound in the aqueous medium (I) during the reaction is not particularly limited as long as the reaction rate is not reduced by the concentration of benzene in the aqueous medium (I) or as long as the nitrile hydratase is not deactivated by the nitrile compound. The percent by weight of the nitrile compound is preferably 50% by weight or less.

The nitrile compound used in the first invention is not particularly limited as long as it is a compound that may be converted to an amide compound by the catalyst having the nitrile hydratase activity in the aqueous medium (I). The representative examples preferably include nitrile compounds having 2 to 4 carbon atoms such as acetonitrile, propionitrile, acrylonitrile, methacrylonitrile, n-butyronitrile, isobutyronitrile, crotononitrile, α-hydroxyisobutyronitrile and the like. More preferably acrylonitrile and methacrylonitrile are used.

Although commercially available nitrile compounds are purified during production, small amounts of impurities are unavoidable. One of the impurities is benzene. For example, benzene is contained in a commercially available acrylonitrile product because the acrylonitrile product is industrially produced by ammoxidation of propylene that contains a small amount of benzene.

The concentration of benzene contained in the aqueous medium (I) may be such that the reduction of the reaction rate is prevented and typically is 4.0 ppm or less and preferably is 2.2 ppm or less. Here, the words the reduction of the reaction rate is prevented mean that the reaction rate is 80% of more relative to the reaction rate (100%) achieved when the benzene concentration in the aqueous medium (I) is not more than 2.2 ppm. In addition, the phrase "the concentration of benzene contained in the aqueous medium (I) is 4.0 ppm or less" means that the amount of benzene contained in 1 kg of the aqueous medium (I) is 4 mg or less. Any process may be used for the process of removing benzene from the nitrile compound or for the process of removing benzene from the aqueous medium (I). For example, there may be mentioned distillation, an adsorption treatment with activated carbon, an adsorption treatment with solid acids such as heteropolyacid that is a superacid and the like, treatment by column chromatography, extraction with sulfolane, biodegradation by microbes capable of assimilating benzene, aeration treatment utilizing volatility of benzene, and the like.

The reaction in the first invention is typically carried out under normal pressure and may be carried out under pressure in order to increase the solubility of the acrylic compound in the aqueous medium (I). In addition, the reaction temperature is not particularly limited and preferably is in a temperature range in which the nitrile hydratase is not deactivated and more preferably 0 to 50° C. On the other hand, pH is not particularly limited as long as the nitrile hydratase activity is maintained and preferably is in the range of pH 5 to pH 10.

The amide-based polymer of the first invention may be produced by homopolymerizing the amide compound obtained as mentioned above or by copolymerizing the amide compound with at least one unsaturated monomer copolymerizable with the amide compound. Here, the amide compound is preferably acrylamide or methacrylamide obtained by the production method for the amide compound of the first invention.

The unsaturated monomers copolymerizable with an amide compound include an unsaturated carboxylic acid such as acrylic acid, methacrylic acid, itaconic acid, maleic acid or fumaric acid, and a salt thereof;
vinylsulfonic acid, styrene sulfonic acid, acrylamidemethylpropane-sulfonic acid, and a salt thereof;
an alkylaminoalkyl ester of (meth)acrylic acid such as N,N-dimethylaminoethylmethacrylate, N,N-diethylaminoethylmethacrylate, N,N-dimethylaminoethylacrylate or the like, and a quaternary ammonium derivative thereof;
N,N-dialkylaminoalkyl(meth)acrylamide such as N,N-dimethylaminopropylmethacrylamide or N,N-dimethylaminopropylacrylamide and, a quaternary ammonium derivative thereof;
a hydrophilic acrylamide such as acetone acrylamide, N,N-dimethylacrylamide, N,N-dimethylmethacrylamide, N-ethylmethacrylamide, N-ethylacrylamide, N,N-diethylacrylamide, N-propylacrylamide and the like;
N-acryloylpyrrolidine, N-acryloylpiperidine and N-acryloylmorpholine;
hydroxyethylmethacrylate, hydroxyethylacrylate, hydroxypropylmethacrylate and hydroxypropylacrylate;
methoxypolyethyleneglycol(meth)acrylate and N-vinyl-2-pyrrolidone;
methacrylamide;
an N-alkyl(meth)acrylamide derivative such as N,N-di-n-propylacrylamide, N-n-butylacrylamide, N-n-hexylacrylamide, N-n-hexylmethacrylamide, N-n-octylacrylamide, N-n-octylmethacrylamide, N-tert-octylacrylamide, N-dodecylacrylamide, N-n-dodecylmethacrylamide or the like;
an N-(ω-glycidoxyalkyl) (meth) acrylamide derivative such as N,N-diglycidylacrylamide, N,N-diglycidylmethacrylamide, N-(4-glycidoxybutyl)acrylamide, N-(4-glycidoxybutyl)methacrylamide, N-(5-glycidoxypentyl)acrylamide, N-(6-glycidoxyhexyl)acrylamide or the like;
a (meth)acrylate derivative such as methyl(meth)acrylate, ethyl(meth)acrylate, butyl(meth)acrylate, lauryl(meth)acrylate, 2-ethylhexyl(meth)acrylate, glycidyl(meth)acrylate or the like;
olefins such as acrylonitrile, methacrylonitrile, vinyl acetate, vinyl chloride, vinylidene chloride, ethylene, propylene, butene and the like; styrene, α-methylstyrene, butadiene, isoprene; and the like.

These monomers may be used alone or two or more kinds in combination.

The polymerization methods for these monomers include, for example, an aqueous solution polymerization, an emulsion polymerization and the like.

Among these, in the case of the aqueous solution polymerization, the total concentration of the amide compound and the optional unsaturated monomer is typically 5 to 90% by weight.

As a polymerization initiator, for example, a radical polymerization initiator may be used.

As the radical polymerization initiators, there may be mentioned a peroxide such as potassium persulfate, ammonium persulfate, hydrogen peroxide, benzoyl peroxide or the like; an azo-based free radical initiator such as azobisisobutyronitrile, 2,2'-azobis(4-amidinopropane)dihydrochloride, sodium 4,4'-azobis(4-cyanovalerate) or the like; and a so-called redox catalyst comprising the above-mentioned peroxides and reducing agents such as sodium bisulfite, triethanolamine, ammonium ferrous sulfate and the like.

The above-mentioned polymerization initiators may be used alone or two or more kinds in combination. The amount of the polymerization initiator is typically 0.001 to 5% by weight, relative to the total amount of the monomers.

In the case of using a single polymerization initiator, the polymerization temperature is typically in the range of 0 to 120° C. and more preferably in the range of 5 to 90° C. In addition, the polymerization temperature is not required to be always kept constant and may be changed accordingly with the progress of the polymerization. Since the polymerization heat will usually generated with the progress of the polymerization to increase the polymerization temperature, cooling may be provided as needed.

The atmosphere during the polymerization is not particularly limited and the polymerization is preferably carried out, for example, under an inert gas atmosphere such as nitrogen gas and the like, from the viewpoint of the smooth polymerization.

The polymerization time is not particularly limited and typically is in the range of 1 to 20 hours.

In addition, the pH of the solution during the polymerization is not particularly limited and the polymerization may be carried out by adjusting the pH as needed. In this case, examples of useful pH adjusters include alkalis such as sodium hydroxide, potassium hydroxide, ammonia and the like; mineral acids such as phosphoric acid, sulfuric acid, hydrochloric acid and the like; organic acids such as formic acid, acetic acid and the like; and others.

The molecular weight of the polymer obtained in the first invention is not particularly limited and typically is in the range of 100,000 to 50,000,000 and preferably in the range of 500,000 to 30,000,000.

The amide-based polymer of the first invention obtained in this way has a good balance between the water solubility and the high molecular weight, and is excellent in hue and may be preferably used as a flocculant, an additive for manufacturing paper, an oil recovery agent, and the like.

2. The Second Invention

Hereinafter, the second invention will be explained in detail.

Firstly, raw materials used in the production method for the acrylamide of the second invention are explained.

[Acrylonitrile]

In the second invention, there is used acrylonitrile having a concentration of acrolein of 1 ppm or less. Here, the phrase "acrylonitrile having a concentration of acrolein of 1 ppm or less" means that the amount of acrolein contained in 1 kg of the acrylonitrile used as a raw material of the second invention is 1 mg or less.

As methods for reducing the concentration of acrolein contained in the acrylonitrile to 1 ppm or less, there may be mentioned a method in which acetylacetone and the like are reacted with acrolein in acrylonitrile and then the reaction product and the acrylonitrile are separated by distillation and the like; a method in which acrolein in acrylonitrile is removed by contact with a porous ion exchange resin having a primary and/or secondary amino group as an exchange group; and a method in which aldehydes substantially consisting of acrolein in acrylonitrile are reduced by contact with a weakly basic ion exchange resin of gel type having a primary and/or secondary amino functional group.

The concentration of acrolein contained in the acrylonitrile may be determined by a gas chromatographic method, a high-performance liquid chromatographic method and the like.

In the second invention, the concentration of acrolein in the acrylonitrile as a raw material is 1 ppm or less but preferably 0.5 ppm or less.

When the concentration of acrolein is within the above range, no inhibition of reaction due to acrolein occurs with respect to the catalytic action by the nitrile hydratase. Further, by using the resulting acrylamide, there may be produced the acrylamide-based polymer which is excellent in hue, has a good balance between the water solubility and the high molecular weight, and is also excellent in quality.

The concentration of acrolein contained in the acrylonitrile used in the second invention is 1 ppm or less, and further the concentration of hydrocyanic acid contained in the acrylonitrile is preferably 5 ppm or less.

Here, the phrase "the concentration of hydrocyanic acid contained in the acrylonitrile is 5 ppm or less" means that the amount of hydrocyanic acid contained in 1 kg of the acrylonitrile used as a raw material of the second invention is 5 mg or less.

As methods of reducing the concentration of hydrocyanic acid contained in the acrylonitrile to 1 ppm or less, for example, as described in Japanese Patent Application Laid-Open Publication No. H11-123098, there may be mentioned a method of removing hydrocyanic acid as a metal complex, a method using an ion exchange resin, a method of causing hydrocyanic acid add to acrylonitrile under alkaline conditions, and the like.

In addition, the concentration of hydrocyanic acid contained in the acrylonitrile may be determined by a titration method using silver nitrate after extracting the acid with an alkaline solution.

In the second invention, the concentration of hydrocyanic acid in the acrylonitrile is preferably 5 ppm or less, more preferably 3 ppm or less and further more preferably 1 ppm or less.

Further, in the second invention, the concentration of acrolein contained in the acrylonitrile is 1 ppm or less and additionally, it is preferable that the concentration of oxazole contained in the acrylonitrile nitrile is 10 ppm or less.

Here, the phrase "the concentration of oxazole contained in the acrylonitrile is 10 ppm or less" means that the amount of oxazole contained in 1 kg of the acrylonitrile used as a raw material of the second invention is 10 mg or less.

As a method of reducing the concentration of oxazole contained in acrylonitrile to 10 ppm or less, there may be mentioned, for example, a method of bringing oxazole in acrylonitrile into contact with an H-type cation exchange resin, as described in Japanese Patent Laid-Open Publication No. S63-118305.

In addition, the concentration of oxazole contained in the acrylonitrile may be determined by a gas chromatographic method, a high-performance liquid chromatographic method and the like.

In the second invention, the concentration of oxazole in the acrylonitrile is preferably 10 ppm or less, more preferably 5 ppm or less and further more preferably 1 ppm or less.

Further, in the second invention, it is preferable that the concentration of acrolein contained in the acrylonitrile used in the second invention is within the above range and the concentration of hydrocyanic acid is 5 ppm or less, preferably 3 ppm or less and more preferably 1 ppm or less, and the concentration of oxazole is 10 ppm or less, preferably 5 ppm or less and more preferably 1 ppm or less.

[Microbial Cell Containing Nitrile Hydratase and the Like]

In the second invention, the acrylamide of the second invention may be obtained by hydrating the above acrylonitrile as a raw material in the presence of a microbial cell containing a nitrile hydratase or a processed product of the microbial cell and the like as a catalyst.

In the second invention, the nitrile hydratase refers to an enzyme having capability of hydrolyzing the nitrile compound to produce a corresponding amide compound. Here, the microbe containing the nitrile hydratase is not particularly limited as long as it produces the nitrile hydratase having capability of hydrolyzing the nitrile compound to produce a corresponding amide compound and maintains a nitrile hydratase activity in an aqueous solution of acrylamide.

Specifically, preferred examples of the above microbes include microbes belonging to *Nocardia, Corynebacterium, Bacillus, thermophilic Bacillus, Pseudomonas, Micrococcus, Rhodococcus* represented by the *rhodochrous* species, *Acinetobacter, Xanthobacter, Rhizobium, Streptomyces, Klebsiella, Enterobacter, Erwinia, Aeromonas, Citrobacter, Achromobacter, Agrobacterium* or *Pseudonocardia* represented by *thermophila* species.

Further, the microbes referred in the second invention also include a transformant obtained by expressing a nitrile hydratase gene cloned from the above-mentioned microbe in an arbitrary host. The arbitrary hosts referred to herein are not particularly limited, and include *Escherichia coli* as a representative example as in the case of Examples described later, *Bacillus* such as *Bacillus subtilis* and the like and other microbial strains such as yeasts, *Actinomyces* and the like. Examples thereof include MT-10822 (the strain deposited at National Institute of Bioscience and Human Technology, Agency of Industrial Science and Technology, Ministry of International Trade and Industry, 1-3, Higashi 1-chome, Tsukuba-shi, Ibaraki-ken, Japan on Feb. 7, 1996, under an accession number FERM BP-5785, under the terms of the Budapest Treaty on the International Recognition of the Deposit of Microorganisms for the Purposes of Patent Procedure). The microbes producing the nitrile hydratase in the second invention also include transformants expressing a mutant nitrile hydratase that are obtained by replacing, deleting, eliminating or inserting one or two or more of constituent amino acids of the enzyme with other amino acids by using recombinant DNA technology and thereby have been further improved in amide compound resistance, nitrile compound resistance and temperature resistance.

In producing an amide compound by using the microbe as mentioned above, the microbial cell or the processed product of the microbial cell is generally used. The microbial cell may be prepared by using a general method which is well known in the fields of molecular biology, bioengineering and genetic engineering. For example, there may be mentioned a method in which the microbe is planted in typical liquid culture mediums such as an LB medium, an M9 medium and the like and then is grown at an appropriate culture temperature (which is generally from 20 to 50° C. and may be 50° C. or higher in the case of a *thermophilic* bacterium), and the microbe is separated and recovered from the culture liquid using a centrifugal separation.

In addition, the processed products of the microbial cells in the second invention include an extract and a ground product of the above microbial cell; a post-separated product obtained by separating and purifying a nitrile hydratase active fraction of the extract and the ground product; and an immobilized product obtained by immobilizing the microbial cell, or the extract, the ground product or the post-separated product of the microbial cell using an appropriate carrier. These are usable as the processed product of the microbial cell of the second invention as long as they have the nitrile hydratase activity. These may be used singly, or in combination of two or more different kinds simultaneously or alternately.

[Aqueous Medium]

The aqueous medium in the second invention refers to water or an aqueous solution containing a buffer such as a phosphate or the like, an inorganic salt such as a sulfate, carbonate or the like, a hydroxide of alkali metal, the amide compound or the like at a suitable concentration. Further, in the present specification, the aqueous medium in the second invention is also referred to as the "aqueous medium (II)".

[Reaction Conditions]

In the second invention, the concentration of the acrylonitrile in the aqueous medium (II) at the start of the reaction is not less than the saturated concentration of the nitrile compound. The upper limit of the concentration is not particularly limited, but when an overly excessive amount of the nitrile compound is supplied, it is required to use a large amount of the catalyst and a reactor having an excessively large volume for completing the reaction, an excessively large heat exchanger for removing heat, and the like. Therefore, economic burden with respect to equipment is increased. For this reason, in the case of acrylamide, the acrylonitrile is preferably supplied such that, when all the acrylonitrile is converted to the corresponding acrylamide, the theoretical concentration of acrylamide in product solution is 40 to 80% by weight. More specifically, the acrylonitrile is supplied in the range of 0.4 to 1.5 parts by weight based on 1.0 part by weight of water.

In addition, the reaction time in the above reaction possibly depends on the conditions such as the amount of the catalyst used, the temperature and the like, and is usually in the range of 1 to 80 hours and is preferably in the range of 2 to 40 hours.

The reactor type is not particularly limited and may be any of a batch system, a semi-batch system and a continuous system. In addition, the reactor type may be any of a suspended bed, a fixed bed or a moving bed. Typically, the reaction is more preferably carried out in a continuous-stirred tank reactor or a plug-flow reactor, and two or more types of reactors may be used in combination.

The amount of the catalyst to be used depends on the reaction conditions, and the type and form of the catalyst, and is usually 10 to 50000 ppm and preferably 50 to 30000 ppm in terms of the weight of dry microbial cell with respect to the weight of the reaction solution.

In addition, the hydration reaction is generally carried out under normal pressure or pressure near normal pressure and may be carried out under increased pressure in order to increase the solubility of the nitrile compound in the aqueous medium (II). Further, the reaction temperature is not particularly limited as long as it is the freezing point or higher of the aqueous medium (II), and the reaction is preferably carried out in the range of 0 to 50° C. and more preferably of 10 to 40° C. Furthermore, the reaction may also be carried out in a slurry state in which products are crystallized in the reaction solution. And, the pH of the reaction solution during the hydration reaction is not particularly limited as long as the nitrile hydratase activity is maintained, and is preferably in the range of pH 6 to 10 and more preferably in the range of pH 7 to 9.

In addition, an amino acid substitute maintaining the nitrile hydratase activity may be obtained by carrying out site-specific mutation. Similar results may be also obtained by constructing a recombinant plasmid by a method other than the site-specific mutation taking into account the specific mutation site and the types of the substituted bases and then introducing the recombinant plasmid into the host cell.

For example, the objective recombinant plasmid may be obtained by synthesizing a DNA fragment having a DNA base sequence in which the base sequence in the mutation site corresponds to a desired such that base sequence to be introduced is the sequence after the substitution of amino acids, by using a DNA synthesizer or the like, and then substituting the fragment for a region of the separately-isolated pPT-DB1 that corresponds to the fragment.

[Acrylamide-Based Polymer]

The acrylamide-based polymer of the second invention may be produced by homopolymerizing the amide compound obtained as mentioned above or by copolymerizing the acrylamide with at least one unsaturated monomer copolymerizable with the acrylamide.

The unsaturated monomers copolymerizable with acrylamide include an unsaturated carboxylic acid such as acrylic acid, methacrylic acid, itaconic acid, maleic acid, fumaric acid or the like, and a salt thereof;

vinylsulfonic acid, styrene sulfonic acid and acrylamidemethylpropane sulfonic acid, and a salt thereof;

an alkylaminoalkyl ester of (meth)acrylic acid such as N,N-dimethylaminoethylmethacrylate, N,N-diethylaminoethylmethacrylate, N,N-dimethylaminoethylacrylate or the like, and a quaternary ammonium derivative thereof;

N,N-dialkylaminoalkyl(meth)acrylamide such as N,N-dimethylaminopropylmethacrylamide, N,N-dimethylaminopropylacrylamide or the like, and a quaternary ammonium derivative thereof;

a hydrophilic acrylamide such as acetone acrylamide, N,N-dimethylacrylamide, N,N-dimethylmethacrylamide, N-ethylmethacrylamide, N-ethylacrylamide, N,N-diethylacrylamide, N-propylacrylamide and the like;

N-acryloylpyrrolidine, N-acryloylpiperidine and N-acryloylmorpholine;

hydroxyethylmethacrylate, hydroxyethylacrylate, hydroxypropylmethacrylate and hydroxypropylacrylate;

methoxypolyethyleneglycol(meth)acrylate and N-vinyl-2-pyrrolidone;

methacrylamide;

an N-alkyl(meth)acrylamide derivative such as N,N-di-n-propylacrylamide, N-n-butylacrylamide, N-n-hexylacrylamide, N-n-hexylmethacrylamide, N-n-octylacrylamide, N-n-octylmethacrylamide, N-tert-octylacrylamide, N-dodecylacrylamide, N-n-dodecylmethacrylamide or the like;

an N-(ω-glycidoxyalkyl)(meth)acrylamide derivative such as N,N-diglycidylacrylamide, N,N-diglycidylmethacrylamide, N-(4-glycidoxybutyl)acrylamide, N-(4-glycidoxybutyl)methacrylamide, N-(5-glycidoxypentyl)acrylamide, N-(6-glycidoxyhexyl)acrylamide or the like;

a (meth)acrylate derivative such as methyl(meth)acrylate, ethyl(meth)acrylate, butyl(meth)acrylate, lauryl(meth)acrylate, 2-ethylhexyl(meth)acrylate, glycidyl(meth)acrylate or the like;

olefins such as acrylonitrile, methacrylonitrile, vinyl acetate, vinyl chloride, vinylidene chloride, ethylene, propylene, butene and the like; styrene, α-methylstyrene, butadiene, isoprene and the like.

These monomers may be used alone or two or more kinds in combination.

The polymerization methods for these monomers include, for example, an aqueous solution polymerization, an emulsion polymerization and the like.

Among these, in the case of the aqueous solution polymerization, the total concentration of acrylamide and the optional unsaturated monomer is typically 5 to 90% by weight.

As a polymerization initiator, for example, a radical polymerization initiator may be used.

As the radical polymerization initiators, there may be mentioned a peroxide such as potassium persulfate, ammonium persulfate, hydrogen peroxide, benzoyl peroxide or the like; an azo-based free radical initiator such as azobisisobutyronitrile, 2,2'-azobis(4-amidinopropane)dihydrochloride, sodium 4,4'-azobis(4-cyanovalerate) or the like; and a so-called redox catalysts comprising the above-mentioned peroxides and a reducing agent such as sodium bisulfite, triethanolamine, ammonium ferrous sulfate and the like.

The above-mentioned polymerization initiators may be used alone or two or more kinds in combination. The amount of the polymerization initiator is typically 0.001 to 5% by weight relative to the total amount of the monomers.

When a single polymerization initiator is used, the polymerization temperature is usually in the range of 0 to 120° C. and preferably in the range of 5 to 90° C. In addition, the polymerization temperature is not required to be always kept constant and may be changed accordingly with the progress of the polymerization. Since the polymerization heat will usually generated with the progress of the polymerization to increase the polymerization temperature, cooling may be provided as needed.

The atmosphere during the polymerization is not particularly limited and the polymerization is preferably carried out, for example, under an inert gas atmosphere such a nitrogen gas and the like, from the viewpoint of the smooth polymerization.

The polymerization time is not particularly limited and usually in the range of 1 to 20 hours.

In addition, the pH of the solution during the polymerization is not particularly limited and the polymerization may be carried out by adjusting the pH as needed. In this case, examples of useful pH adjusters include alkalis such as sodium hydroxide, potassium hydroxide, ammonia and the like; mineral acids such as phosphoric acid, sulfuric acid, hydrochloric acid and the like; organic acids such as formic acid, acetic acid and the like; and others.

The molecular weight of the polymer obtained from the second invention is not particularly limited and is typically in the range of 100,000 to 50,000,000 and preferably in the range of 500,000 to 30,000,000.

The amide-based polymer of the second invention obtained in this way has a good balance between the water solubility and the high molecular weight and is furthermore excellent in hue, and may be used as a flocculant, an additive for manufacturing paper, an oil recovery agent and the like.

EXAMPLES

Hereinafter, the present invention will be explained in more detail with reference to the Examples, but the present invention is not limited by these Examples.

1. Examples of the First Invention

The concentration of benzene was measured according to gas chromatographic analysis. The gas chromatographic analysis was carried out by using G-950 1.2 mm×40 m (25 μm) manufactured by Chemicals Evaluation and Research Institute, Japan as a column. Helium was used as a carrier gas and a FID detector was used for the analysis.

In addition, the HPLC analysis in each of Examples and Comparative Examples was carried out by using Finepak SIL C18-5 (250×4.6 φmm) manufactured by JASCO Corporation as a column and a 10 mM phosphoric acid aqueous solution containing 4% by volume of acetonitrile as a developer. Further, acrylamide and methacrylamide were detected by the absorbance at 220 nm.

Production Example 1-1

To a reaction vessel was charged an adsorbent of an activated carbon fixed bed containing 1 kg of an activated carbon (internal surface area: 1000 m$^2$/kg). An acrylonitrile a having a concentration of benzene of 26 ppm was pumped through the adsorbent from the bottom to the top at a flow rate of 200 m/hr at a temperature of 10° C. After the acrylonitrile a passed through the adsorbent, the concentration of benzene in the acrylonitrile was measured to be 4.0 ppm. Hereinafter, the acrylonitrile after the activated carbon absorption treatment is referred to as the acrylonitrile b.

Production Example 1-2

Acrylonitrile c having a concentration of benzene of 11 ppm was used as it is.

Production Example 1-3

Methacrylonitrile having a concentration of benzene of 8 ppm was used as it is.

Preparation of Microbial Cell

Preparation Example 1-1

Culture of Microbial Cell Containing Nitrile Hydratase Derived from *Pseudonocardia Thermophila* JCM3095

A culture medium with a volume of 100 ml having the composition shown in the medium composition 1-1 was prepared in a 500-milliliter Erlenmeyer flask fitted with a baffle, and was sterilized in an autoclave at 121° C. for 20 minutes. Thereafter, ampicillin was added to this medium so that the final concentration was 50 μg/ml. 30 flasks were prepared in the same manner. One loopful of MT-10822 strain (FERM BP-5785) was inoculated into each Erlenmeyer flask fitted with a baffle and the resultant medium was incubated at 37° C. at 130 rpm for 20 hours. The culture solutions in Erlenmeyer flasks fitted with a baffle were collected and only the microbial cell was separated from the collected culture solution through centrifugation (15000 G×15 minutes). Subsequently, the microbial cell was resuspended in 50 ml of a physiological saline solution and then the wet microbial cell was obtained through recentrifugation.

[Medium Composition 1-1]

| | |
|---|---|
| Yeast extract | 5.0 g/liter |
| Polypeptone | 10.0 g/liter |
| NaCl | 5.0 g/liter |
| Cobalt chloride hexahydrate | 10.0 mg/liter |
| Ferric sulfate heptahydrate | 40.0 mg/liter |
| pH 7.5 | |

Preparation Example 1-2

Culture of Microbial Cell Containing Nitrile Hydratase Derived from *Rhodococcus rhodochrous* J-1

Wet microbial cell was obtained by using *Rhodococcus rhodochrous* J-1 strain described in Japanese Unexamined Patent Application Publication No. H06-55148 (the strain deposited at the above-mentioned deposition agency under an accession number FERM BP-1478, under the terms of the Budapest Treaty on the International Recognition of the Deposit of Microorganisms for the Purposes of Patent Procedure and is subdivided to all persons upon request).

A culture medium with a volume of 100 ml having the composition shown in the medium composition 1-2 was prepared into a 500-milliliter Erlenmeyer flask fitted with a baffle, and was sterilized in an autoclave at 121° C. for 20 minutes. To this medium was inoculated one loopful of *Rhodococcus rhodochrous* J-1 strain described in Japanese Patent Application Publication No. H06-55148 (the strain deposited at the above-mentioned deposition agency under an accession number FERM BP-1478, under the terms of the Budapest Treaty on the International Recognition of the Deposit of Microorganisms for the Purposes of Patent Procedure and is subdivided to all persons upon request) and incubated at 30° C. at 130 rpm for 72 hours. Only the microbial cell was separated from the culture solution through centrifugation (15000 G×15 minutes). Subsequently, the microbial cell was resuspended in 50 ml of a physiological saline solution and then the wet microbial cell was obtained through recentrifugation.

[Culture Medium Composition 1-2]

| | |
|---|---|
| Glucose | 10.0 g/L |
| Potassium dihydrogen phosphate | 0.5 g/L |
| Dipotassium hydrogen phosphate | 0.5 g/L |
| Magnesium sulfate heptahydrate | 0.5 g/L |
| Yeast extract | 1.0 g/L |
| Peptone | 7.5 g/L |
| Urea | 7.5 g/L |
| Cobalt chloride hexahydrate | 10.0 mg/L |
| pH 7.2 | |

Example 1-1

Conversion of Nitrile Compound into Amide Compound (1)

The wet microbial cell obtained in Preparation Example 1-1 was appropriately diluted with a 20 mM Tris-HCl buffer solution (pH 7.5). To the resulting solution was added the acrylonitrile b described in Production Example 1-1 so that the concentration of acrylonitrile in the whole reaction solution was 20% by weight and then the resultant mixture was reacted at 20° C. for 10 minutes. Here, the concentration of benzene in the aqueous medium (I) (the whole reaction solution) was 0.8 ppm. After the reaction, an equivalent weight of a 1 M phosphoric acid aqueous solution based on the reaction solution was added to the reaction solution to stop the reaction, and the concentration of the resulting acrylamide was measured by HPLC analysis. Subsequently, the production rate (=the reaction rate) of acrylamide per unit wet microbial cell and per unit reaction time was calculated. The results are shown in Table 1-1. The reaction rate obtained was set as 100% and compared with those of Example 1-2, Example 1-3, Comparative Example 1-1 and Comparative Example 1-2.

Example 1-2

Conversion of Nitrile Compound into Amide Compound (2)

The wet microbial cell obtained in Preparation Example 1-1 was appropriately diluted with a 20 mM Tris-HCl buffer solution (pH 7.5). To the resulting solution was added the acrylonitrile c described in Production Example 1-2 so that the concentration of acrylonitrile was 20% by weight and the resultant mixture was reacted at 20° C. for 10 minutes. Here, the concentration of benzene in the aqueous medium (I) was 2.2 ppm. Thereafter, the procedures were performed in the same manner as in Example 1-1. The results are shown in Table 1-1.

Example 1-3

Conversion of Nitrile Compound into Amide Compound (3)

The concentration of benzene in acrylonitrile was adjusted to be 20 ppm by adding benzene to the acrylonitrile b described in Production Example 1-1. The procedures were performed in the same manner as in Example 1-1 except that the acrylonitrile to be used was replaced by the acrylonitrile as described above. Here, the concentration of benzene in the aqueous medium (I) was 4.0 ppm. The results are shown in Table 1-1.

Comparative Example 1-1

Conversion of Nitrile Compound into Amide Compound (1)

The procedures were performed in the same manner as in Example 1-1 except that the acrylonitrile to be used was replaced by the acrylonitrile a described in Production Example 1-1. Here, the concentration of benzene in the aqueous medium (I) was 5.2 ppm. The results are shown in Table 1-1.

Comparative Example 1-2

Conversion of Nitrile Compound into Amide Compound (2)

The concentration of benzene in acrylonitrile was adjusted to be 26 ppm by adding benzene to the acrylonitrile b described in Production Example 1-1. The procedures were performed in the same manner as in Example 1-1 except that the acrylonitrile to be used was replaced by the acrylonitrile as described above. Here, the concentration of benzene in the aqueous medium (I) was 5.2 ppm. The results are shown in Table 1-1.

From the Table 1-1, it is found that the decrease of reaction rate may be prevented by controlling the concentration of benzene in the aqueous medium (I) to 4.0 ppm or less and a substance causing the decrease of reaction rate is benzene.

Example 1-4

Conversion of Nitrile Compound into Amide Compound (4)

The procedures were performed in the same manner as in Example 1-1 except that the wet microbial cell to be used was replaced by the wet microbial cell obtained in Preparation Example 1-2. The results are shown in Table 1-2. The reaction rate obtained was set as 100% and compared with those of Example 1-5 and Comparative Example 1-3, by setting the reaction rate obtained as 100%.

Example 1-5

Conversion of Nitrile Compound into Amide Compound (5)

The procedures were performed in the same manner as in Example 1-3 except that the wet microbial cell to be used was replaced by the wet microbial cell obtained in Preparation Example 1-2. The results are shown in Table 1-2.

Comparative Example 1-3

Conversion of Nitrile Compound into Amide Compound (3)

The procedures were performed in the same manner as in Comparative Example 1-1 except that the wet microbial cell to be used was replaced by the wet microbial cell obtained in Preparation Example 1-2. The results are shown in Table 1-2.

Example 1-6

Conversion of Nitrile Compound into Amide Compound (6)

The wet microbial cell obtained in Preparation Example 1-1 was appropriately diluted with a 20 mM Tris-HCl buffer solution (pH 7.5). To the resulting solution was added the methacrylonitrile described in Production Example 1-3 so that the concentration of methacrylonitrile was 20% by weight and the resultant mixture was reacted at 20° C. for 10 minutes. Here, the concentration of benzene in the aqueous medium (I) was 1.6 ppm. After the reaction, an equivalent weight of a 1M phosphoric acid aqueous solution based on the reaction solution was added to the reaction solution to stop the reaction, and the concentration of the resulting methacrylamide was measured by HPLC analysis. Subsequently, the production rate (=the reaction rate) of methacrylamide per unit wet microbial cell and per unit reaction time was calculated. The results are shown in Table 1-3. The reaction rate obtained was set as 100% and compared with those of Example 1-7 and Comparative Example 1-4.

Example 1-7

Conversion of Nitrile Compound into Amide Compound (7)

The concentration of benzene in methacrylonitrile was adjusted to be 20 ppm by adding benzene to the methacrylonitrile described in Production Example 1-3. The procedures were performed in the same manner as in Example 1-6 except that the methacrylonitrile to be used was replaced by the methacrylonitrile as described above. Here, the concentration of benzene in the aqueous medium (I) was 4.0 ppm. The results are shown in Table 1-3.

Comparative Example 1-4

Conversion of Nitrile Compound into Amide Compound (4)

The concentration of benzene in methacrylonitrile was adjusted to be 25 ppm by adding benzene to the methacrylonitrile described in Production Example 1-3. The procedures were performed in the same manner as in Example 1-6 except that the methacrylonitrile to be used was replaced by the methacrylonitrile as described above. Here, the concentration of benzene in the aqueous medium (I) was 5.0 ppm. The results are shown in Table 1-3.

Example 1-8

Conversion of Nitrile Compound into Amide Compound (8)

The procedures were performed in the same manner as in Example 1-6 except that the wet microbial cell to be used was replaced by the wet microbial cell obtained in Preparation Example 1-2. The results are shown in Table 1-4. The reaction rate obtained was set as 100% and compared with those of Example 1-9 and Comparative Example 1-5, by setting the reaction rate obtained as 100%.

Example 1-9

Conversion of Nitrile Compound into Amide Compound (9)

The procedures were performed in the same manner as in Example 1-7 except that the wet microbial cell to be used was replaced by the wet microbial cell obtained in Preparation Example 1-2. The results are shown in Table 1-4.

Comparative Example 1-5

Conversion of Nitrile Compound into Amide Compound (5)

The procedures were performed in the same manner as in Comparative Example 1-4 except that the wet microbial cell to be used was replaced by the wet microbial cell obtained in Preparation Example 1-2. The results are shown in Table 1-4.

TABLE 1-1

|  | Concentration of benzene in aqueous medium (I) (ppm) | Relative Reaction Rate (%) |
| --- | --- | --- |
| Example 1-1 | 0.8 | 100 |
| Example 1-2 | 2.2 | 100 |
| Example 1-3 | 4.0 | 84 |
| Comparative Example 1-1 | 5.2 | 69 |
| Comparative Example 1-2 | 5.2 | 70 |

Nitrile compound used: Acrylonitrile
Microbial cell used: Microbial cell containing the nitrile hydratase derived from *Pseudonocardia thermophila*

TABLE 1-2

| | Concentration of benzene in aqueous medium (I) (ppm) | Relative Reaction Rate (%) |
|---|---|---|
| Example 1-4 | 0.8 | 100 |
| Example 1-5 | 4.0 | 85 |
| Comparative Example 1-3 | 5.2 | 72 |

Nitrile compound used: Acrylonitrile
Microbial cell used: Microbial cell containing a nitrile hydratase derived from *Rhodococcus rhodochrous*

TABLE 1-3

| | Concentration of benzene in aqueous medium (I) (ppm) | Relative Reaction Rate (%) |
|---|---|---|
| Example 1-6 | 1.6 | 100 |
| Example 1-7 | 4.0 | 83 |
| Comparative Example 1-4 | 5.0 | 66 |

Nitrile compound used: Methacrylonitrile
Microbial cell used: Microbial cell containing a nitrile hydratase derived from *Pseudonocardia thermophila*

TABLE 1-4

| | Concentration of benzene in aqueous medium (I) (ppm) | Relative Reaction Rate (%) |
|---|---|---|
| Example 1-8 | 1.6 | 100 |
| Example 1-9 | 4.0 | 85 |
| Comparative Example 1-5 | 5.0 | 68 |

Nitrile compound used: Methacrylonitrile
Microbial cell used: Microbial cell containing a nitrile hydratase derived from *Rhodococcus rhodochrous*

Example 1-10

Production of Acrylamide

There were prepared a 1-liter glass flask equipped with a stirrer as a first reactor and a Teflon (trademark) tube with an inside diameter of 5 mm and a length of 20 m as a second reactor. To the first reactor was charged 400 g of water in advance.

In accordance with the method described in Japanese Patent Application Laid-Open Publication No. 2001-340091, a microbial cell containing a nitrile hydratase was cultured and the resulting wet microbial cell was suspended in a 0.3 mM-NaOH aqueous solution. The suspension and the acrylonitrile b were continuously fed into the first reactor under stirring at a rate of 49 g/h and 31 g/h, respectively. In addition, the reaction solution was continuously taken out from the first reactor at a rate of 80 g/h so that the liquid level of the first reactor was maintained constant. The liquid taken out was continuously fed into the second reactor at a rate of 80 g/h and the reaction was further performed in the second reactor.

Both the first and second reactors were immersed in a water bath at a temperature of 10 to 20° C. to control the liquid temperature in each reactor at 15° C.

The amount of the wet microbial cell added to the 0.3 mM-NaOH aqueous solution was adjusted so that the conversion rate to acrylamide at the outlet of the first reactor was 90% or higher and the concentration of acrylonitrile at the outlet of the second reactor was at the detection limit or less (100 ppm or less). The conversion rate to acrylamide was determined by the analysis of HPLC.

As a result, the objective conversion rate was achieved when the wet microbial cell was 2.5% by weight based on the 0.3 mM-NaOH aqueous solution.

Comparative Example 1-6

The procedures were performed in the same manner as in Example 1-10 except that the acrylonitrile to be used was replaced by the acrylonitrile a. As a result, the added amount of the wet microbial cell required for achieving the objective conversion rate was 3.0% by weight of the wet microbial cell based on the 0.3 mM-NaOH aqueous solution. The added amount of the wet microbial cell was larger than that in the case of Example 1-10 and the inhibition of reaction by benzene was confirmed.

Comparative Example 1-7

The concentration of benzene in acrylonitrile was adjusted to be 26 ppm by adding benzene to the acrylonitrile b. The procedures were performed in the same manner as in Example 1-10 except that the acrylonitrile to be used was replaced by the acrylonitrile as described above. As a result, the added amount of the wet microbial cell required for achieving the objective conversion rate was 3.0% by weight of the microbial cell based on the 0.3 mM-NaOH aqueous solution. The added amount of the wet microbial cell was larger than that in the case of Example 1-10 and the inhibition of reaction by benzene was confirmed.

Example 1-11

The reaction solution of Example 1-10 was treated with an activated carbon under acidic conditions (pH 5), and then the wet microbial cell was removed. The resulting reaction solution was neutralized with 1 N-NaOH to obtain an aqueous solution of 50% by weight of acrylamide.

Water was added to the resulting aqueous solution of acrylamide to obtain an aqueous solution of 20% by weight of acrylamide. To a 1 liter polyethylene vessel was added 500 g of the aqueous solution of 20% by weight of acrylamide and the dissolved oxygen in the solution was removed by passing nitrogen while maintaining the temperature at 18° C., and the resulting solution was immediately placed in a heat-insulating block made of expanded polystyrene foam.

Subsequently, three solutions were prepared by dissolving $200 \times 10^{-6}$ mpm (a molar ratio to acrylamide) of sodium 4,4'-azobis-4-cyanovalerate, $200 \times 10^{-6}$ mpm of dimethylaminopropionitrile and $80 \times 10^{-6}$ mpm of ammonium persulfate each in a small amount of water and then were promptly poured into the 1 liter polyethylene vessel in this order. To these reagents, a nitrogen gas had been purged in advance. During the pouring of these reagents, and before and after the pouring of these reagents, a small amount of the nitrogen gas was purged into the above-mentioned polyethylene vessel to prevent an oxygen gas from being mixed into the solution.

After an induction period of several minutes subsequent to the pouring of the reagents, the feeding of nitrogen gas was stopped because the internal temperature of the polyethylene vessel was observed to rise. The polyethylene vessel was kept as it is in the heat-insulating block for approximately 100 minutes, and consequently the internal temperature of the polyethylene vessel reached approximately 70° C. The polyethylene vessel was then taken out from the heat-insulating block and immersed in water at 97° C. for 2 hours to further perform the polymerization reaction. Thereafter, the polyethylene vessel was immersed in cold water to cool and stop the polymerization reaction.

The thus obtained water-containing gel of an acrylamide polymer was taken out from the polyethylene vessel, divided into small pieces, and ground through a mincer. The ground water-containing gel of the acrylamide polymer was dried with hot air at 100° C. for 2 hours and further ground by a high-speed rotary blade grinder to obtain a dried powderly acrylamide polymer. The resulting dried powderly acrylamide polymer was sieved to collect the powder that passed through 32- to 42-mesh screens. Thus, a polymer sample for a subsequent test was obtained.

Comparative Example 1-8

In the same manner as in Example 1-11, an aqueous solution of 20% by weight of acrylamide was obtained from the reaction solution obtained in Comparative Example 1-6, and a polymer sample was obtained by using the aqueous solution of the acrylamide.

Comparative Example 1-9

In the same manner as in Example 1-11, an aqueous solution of 20% by weight of acrylamide was obtained from the reaction solution obtained in Comparative Example 1-7, and a polymer sample was obtained by using the aqueous solution of the acrylamide.

<Testing Methods of Acrylamide Polymer>

The evaluations were performed on the hue of the polymer samples obtained in the above Example 1-11, Comparative Example 1-8 and Comparative Example 1-9 by the following methods.

Water Solubility: Into a 1 liter beaker was poured 600 ml of water and 0.66 g of the polymer sample (net content: 0.6 g) was added while the water stirring at 25° C. by using a stirring blade having a defined shape, followed by stirring at 400 rpm for 2 hours. The resulting solution was filtered through a 150-mesh metal wire screen. The water solubility of the polymer sample was judged from the amount of insoluble component and the filterability. In detail, the evaluation was made as follows. Excellent: Completely dissolved; Good: Almost completely dissolved; Do: Insoluble component was present but separated by filtration; and Poor: The passing of the filtrate was so slow that filtration of insoluble component was practically impossible.

Hue: With the hue of the polymer, the polymer powders were visually evaluated.

The evaluation results are shown in Table 1-5.

TABLE 1-5

|  | Concentration of benzene in aqueous medium (I) | Water Solubility of Polymer | Hue of Polymer (Visual Observation) |
|---|---|---|---|
| Example 1-11 | 2 ppm | Excellent | White |
| Comparative Example 1-8 | 10 ppm | Do | Light yellow |
| Comparative Example 1-9 | 10 ppm | Do | Light yellow |

2. Examples of the Second Invention

Hereinafter, unless otherwise specified, % and ppm are by weight.

Example 2-1

Culture of Microbial Cell Containing Nitrile Hydratase

In accordance with the method described in Japanese Patent Application Laid-open Publication No. 2001-340091, a microbial cell containing a nitrile hydratase was cultured to obtain a wet microbial cell.

[Purification of Acrylonitrile]

First, 0.3 liter of Diaion WA-20 (trade name, manufactured by Mitsubishi Kasei Corporation), a resin having a primary and/or secondary amino group, was washed with water. The resin was then filled in a column made of SUS-304 having an inside diameter of 40 mm and a length of 400 mm. An acrylonitrile containing 2 ppm of acrolein was passed through the column at a flow rate of 6 l/hr. The concentration of acrolein in the purified acrylonitrile after passing through the column was determined by the following high-performance liquid chromatographic method (the lower detection limit was 0.1 ppm) to be 0.9 ppm.

Analysis Conditions:

High-performance liquid chromatographic apparatus: LC-6A System (Manufactured by Shimadzu Corporation) (UV detector wavelength: 210 nm, Column temperature: 40° C.)

Separation column: L-Column ODS Type-Waters (manufactured by Chemicals Inspection and Testing Institute) (Column size: 4.6 mm×250 mm)

Eluent: 20% (by volume) acetonitrile aqueous solution (Adjusted to pH 2.5 with phosphoric acid)

[Production of Acrylamide]

There were prepared a 1-liter glass flask equipped with a stirrer as a first reactor and a Teflon (trademark) tube with an inside diameter of 5 mm and a length of 20 m as a second reactor. To the first reactor was charged 400 g of water in advance.

The wet microbial cell obtained by the above culture method was suspended in a 0.3 mM-NaOH aqueous solution. The suspension and the acrylonitrile were continuously fed into the first reactor under stirring at a rate of 49 g/h and 31 g/h, respectively. In addition, the reaction solution was continuously taken out from the first reactor at a rate of 80 g/h so that the liquid level of the first reactor was maintained constant. The liquid taken out was continuously fed into the second reactor and the reaction was further performed in the second reactor.

Both the first and second reactors were immersed in a water bath at a temperature of 10 to 20° C. to control the liquid temperature in each reactor at 15° C.

The added amount of the wet microbial cell to the 0.3 mM-NaOH aqueous solution was adjusted so that the conversion rate to acrylamide at the outlet of the first reactor was 90% or more and the concentration of acrylonitrile at the outlet of the second reactor at the detection limit or less (100 ppm or less). The conversion rate to acrylamide was determined by the analysis of HPLC.

As a result, the objective conversion rate was achieved when the wet microbial cell was 2.5% by weight based on the 0.3 mM-NaOH aqueous solution.

Comparative Example 2-1

The procedures were performed in the same manner as in Example 2-1 except that as a raw material, the acrylonitrile was used without being subjected to the ion exchange treatment. As a result, the added amount of the wet microbial cell required for achieving the objective conversion rate was 2.8% by weight of the wet microbial cell based on the 0.3 mM-NaOH aqueous solution. The added amount of the wet microbial cell was larger than that in the case of Example 2-1 and the inhibition of reaction by acrolein was confirmed.

Example 2-2

The concentration of acrolein in acrylonitrile was adjusted to be 2 ppm by adding acrolein to the purified acrylonitrile obtained in Example 2-1. Acrylamide was produced using the acrylonitrile in the same manner as in Example 2-1. As a result, the added amount of the wet microbial cell required for achieving the objective conversion rate was 2.8% by weight of the wet microbial cell based on the 0.3 mM-NaOH aqueous solution. The added amount of the wet microbial cell was larger than that in the case of Example 2-1 and the inhibition of reaction by acrolein was confirmed.

Comparative Example 2-2

The reaction solution of Example 2-1 was treated with activated carbon under acidic conditions (pH 5), and then the wet microbial cell was removed. The resulting reaction solution was neutralized with 1 N-NaOH to obtain an aqueous solution of 50% by weight of acrylamide.

Water was added to the resulting acrylamide solution to obtain an aqueous solution of 20% by weight of acrylamide. To a 1 liter polyethylene vessel was added 500 g of the aqueous solution of 20% by weight of acrylamide and the dissolved oxygen in the solution was removed by passing nitrogen while maintaining the temperature at 18° C. and the resulting solution was immediately placed in a heat-insulating block made of expanded polystyrene foam.

Subsequently, three solutions were prepared by dissolving $200 \times 10^{-6}$ mpm (a molar ratio to acrylamide) of sodium 4,4'-azobis-4-cyanovalerate, $200 \times 10^{-6}$ mpm of dimethylaminopropionitrile and $80 \times 10^{-6}$ mpm of ammonium persulfate each in a small amount of water and then were promptly poured into the 1 liter polyethylene vessel in this order. To these reagents, a nitrogen gas had been purged in advance. During the pouring of these reagents, and before and after the pouring of these reagents, a small amount of the nitrogen gas was purged into the above-mentioned polyethylene vessel to prevent an oxygen gas from being mixed into the solution.

After an induction period of several minutes subsequent to the pouring of the reagents, the feeding of nitrogen gas was stopped because the internal temperature of the polyethylene vessel was observed to rise. The polyethylene vessel was kept as it is in the heat-insulating block for approximately 100 minutes, and consequently the internal temperature of the polyethylene vessel reached approximately 70° C. The polyethylene vessel was then taken out from the heat-insulating block and immersed in water at 97° C. for 2 hours to further perform the reaction. Thereafter, the polyethylene vessel was immersed in cold water to cool and stop the polymerization reaction.

The thus obtained water-containing gel of an acrylamide polymer was taken out from the polyethylene vessel, divided into small pieces, and ground through a mincer. The ground water-containing gel of the acrylamide polymer was dried with hot air at 100° C. for 2 hours and further ground by a high-speed rotary blade grinder to obtain a dried powderly acrylamide. The resulting dried powderly acrylamide polymer was sieved to collect the powder that passed through 32- to 42-mesh screens. Thus, a polymer sample for a subsequent test was obtained.

Example 2-3

The purified acrylonitrile used in Example 2-1 was further passed through a column made of SUS-304 having an inside diameter of 40 mm and a length of 400 mm in which 0.3 liter of Diaion WA-20 washed with water was filled at a flow rate of 6 l/hr. The concentration of acrolein in the purified acrylonitrile after passing through the column was 0.4 ppm.

An aqueous solution of 20% by weight of acrylamide was obtained using the acrylonitrile in the same manner as in Example 2-1 and Example 2-2, and a polymer sample was obtained by using the aqueous solution of the acrylamide.

Comparative Example 2-3

An aqueous solution of 20% by weight of acrylamide was obtained from the reaction solution obtained in Comparative Example 2-1 in the same manner as in Example 2-2, and a polymer sample was obtained by using the aqueous solution of the acrylamide.

Comparative Example 2-4

An aqueous solution of 20% by weight of acrylamide was obtained from the reaction solution obtained in Comparative Example 2-2 in the same manner as in Example 2-2, and a polymer sample was obtained by using the aqueous solution of the acrylamide.

<Testing Methods of Acrylamide Polymer>

For the polymer samples obtained in the above Example 2-2, Example 2-3 and Comparative Example 2-2, the evaluation of water solubility, measurement of the standard viscosity and evaluation of hue were performed using the following methods.

Water Solubility: Into an 1 liter beaker was placed 600 ml of water and 0.66 g of the polymer sample (net content: 0.6 g) was added while the water stirring at 25° C. by using a stirring blade having a defined shape, followed by stirring at 400 rpm for 2 hours. The resulting solution was filtered through a 150-mesh metal wire screen. The water solubility of the polymer sample was judged from the amount of insoluble component and the filterability. In detail, the evaluation was made as follows. Excellent: Completely dissolved; Good: Almost completely dissolved; Do: Insoluble component was present but separated by filtration; and Poor: The passing of the filtrate was so slow that filtration of insoluble component was practically impossible.

Standard viscosity: The filtrate obtained in the above water solubility test was an aqueous polymer solution having a concentration of 0.1% by weight. To the aqueous polymer solution was added sodium chloride with a concentration equivalent to 1 M. By using a BL-type viscometer equipped with a BL adapter, the viscosity (standard viscosity) of the resulting solution was measured at 25° C. and a rotor revolution speed of 60 rpm. The standard viscosity obtained in this manner is commonly employed as a value correlated with the molecular weight.

Hue: With the hue of the polymer, the polymer powders were visually evaluated.

The evaluation results are shown in Table 2-1.

TABLE 2-1

|  | Concentration of Acrolein in Raw Material Acrylonitrile | Water Solubility of Polymer | Viscosity of Polymer Aqueous Solution (mPa·s) | Hue of Polymer (Visual Observation) |
|---|---|---|---|---|
| Example 2-2 | 0.9 ppm | Good | 5.8 | White |
| Example 2-3 | 0.4 ppm | Excellent | 5.8 | White |
| Comparative Example 2-3 | 2 ppm | Poor | No measurement done* | Light Yellow |
| Comparative Example 2-4 | 2 ppm | Poor | No measurement done* | Light Yellow |

*The viscosity of the filtrate is impossible to be measured because the passing of the filtrate was slow and the filtration was practically impossible.

INDUSTRIAL APPLICABILITY

According to the first invention, since a corresponding amide compound may be efficiently produced from a nitrile compound by the reaction using a nitrile hydratase, the present invention is useful for industrially performing the production of the amide compound.

The invention claimed is:

1. A method for producing an acrylamide, comprising hydrating an acrylonitrile treated with an ion exchange resin having a primary and/or secondary amino group that has been washed with water and having an acrolein concentration of 1 ppm or less by a microbial cell containing a nitrile hydratase or a processed product of the microbial cell in an aqueous medium.

2. A method for producing an acrylamide-based polymer, comprising homopolymerizing the acrylamide according to claim 1 or copolymerizing the acrylamide and at least one unsaturated monomer copolymerizable with the acrylamide.

* * * * *